US009725391B2

(12) United States Patent
Lee et al.

(10) Patent No.: US 9,725,391 B2
(45) Date of Patent: Aug. 8, 2017

(54) SYNTHETIC METHOD OF ENANTIOMERICALLY PURE 2,2'-DIHYDROXY-1,1'-BINAPHTHYL-3-CARBOXYLIC ACID

(75) Inventors: Hyunil Lee, Gyeonggi-do (KR); Heungsik Yoon, Gyeonggi-do (KR); Young Hee Lee, Gyeonggi-do (KR); Heejung Jung, Gyeonggi-do (KR); Young-Kook Koh, Gyeonggi-do (KR)

(73) Assignee: Aminologics Co., Ltd., Seoul (KR)

( * ) Notice: Subject to any disclaimer, the term of this patent is extended or adjusted under 35 U.S.C. 154(b) by 713 days.

(21) Appl. No.: 13/990,020

(22) PCT Filed: Nov. 24, 2011

(86) PCT No.: PCT/KR2011/009034
§ 371 (c)(1),
(2), (4) Date: Jan. 23, 2014

(87) PCT Pub. No.: WO2012/070896
PCT Pub. Date: May 31, 2012

(65) Prior Publication Data
US 2014/0142336 A1 May 22, 2014

(30) Foreign Application Priority Data
Nov. 26, 2010 (KR) .................. 10-2010-0118975

(51) Int. Cl.
*C07C 63/36* (2006.01)
*C07C 51/02* (2006.01)
*C07B 57/00* (2006.01)
*C07C 51/41* (2006.01)
*C07C 51/43* (2006.01)

(52) U.S. Cl.
CPC ............. *C07C 51/02* (2013.01); *C07B 57/00* (2013.01); *C07C 51/412* (2013.01); *C07C 51/43* (2013.01); *C07B 2200/07* (2013.01)

(58) Field of Classification Search
CPC .................................................. C07C 63/36
USPC ........................................................ 562/490
See application file for complete search history.

(56) References Cited

U.S. PATENT DOCUMENTS

2006/0173211 A1* 8/2006 Kim et al. .................... 562/439
2014/0012038 A1* 1/2014 Chang et al. ................. 562/439

FOREIGN PATENT DOCUMENTS

| EP | 2643284 A4 | 8/2014 |
| JP | 2003-327559 A | 11/2003 |
| KR | 10-0208867 B1 | 7/1999 |
| KR | 10-0661280 B1 | 12/2006 |
| KR | 10-2010-0039114 A | 4/2010 |
| KR | 10-2010-0054628 A | 5/2010 |
| KR | 101270586 B1 | 6/2013 |
| WO | 2004060850 A1 | 7/2004 |
| WO | 2012070896 A2 | 5/2012 |
| WO | 2012070896 A3 | 7/2012 |

OTHER PUBLICATIONS

Czechoslovakian Patent Invention No. 9,600,064A3 (*Vyosoka Skola Chem Tech* [CZ] vs *Chemicko Technologicka* [CZ]), dated May 13, 1998, and English translation. CZ9600064A3 is also published as CZ287879B6.
Hovorka, M. et al., Chiral Tridentate Ligands Based on 3-Substituted Binaphthols and Derived Complex Hydrides of Aluminum, Pure & Appl. Chem., 1998, vol. 70, pp. 415-418, See Figures 2-3.
International Search Report and Written Opinion dated May 29, 2012, regarding PCT/KR2011/009034.
Fogassy, Elemer et al., "Optical Resolution Methods," Organic & Biomolecular Chemistry 2006, vol. 4, pp. 3011-3030, see Section 3.1.1.2 in p. 3014.
Supplementary material of Xiong, Xiao-Feng et al., "Merging Chiral Organocatalysts: Enantio- and Diastereoselective Direct Vinylogous Mannich Reaction of Allcylimines," Chem. Comm. 2009, pp. 6994-6996, see p. S2.
Molnar, Peter et al., Influence of Benzylamine on the Resolution of Ibuprofen with (+)-(R)-Phenylethylamine via Supercritical Fluid Extraction, Chirality 2009, vol. 21, pp. 628-636, See abstract; Figure 1.
H. Park, K.M. Kim, A. Lee, S. Ham, W. Nam, J. Chin, "Bioinspired Chemical Inversion of L-Amino Acids to D-Amino Acids", J. Amer. Chem. Soc. 2007, 129, pp. 1518-1519.
K.M. Kim, H. Park, H. Kim, J Chin, W. Nam, "Enantioselective Recognition of 1, 2-Amino Alcohols by Reversible Formation of Imines with Resonance-Assisted Hydrogen Bonds", Org. Lett. Published Jul. 7, 2005, pp. 3525-3527.
Hovorka, M., et al., Czech Rep. 2001, CZ287879B6 (also published as CZ9600064A3).
International Preliminary Report on Patentability dated May 28, 2013, and Written Opinion dated May 29, 2012 regarding PCT/KR2011/009034.
Supplementary European Search Report and Search Opinion dated Jul. 3, 2014, regarding EP11842877.
Holakovsky et al.; "Preparation of New Binaphthol-Based Tridentate Ligands or Enatioselective Synthesis", Collection of Czechoslovak Chemical Communications, vol. 5, 2000, p. 805-815, XP8168196.

(Continued)

*Primary Examiner* — Yong Chu
*Assistant Examiner* — Sonya Wright
(74) *Attorney, Agent, or Firm* — Arent Fox LLP

(57) ABSTRACT

The present invention relates to a method for preparing enantiomerically pure compounds 1a and 1b of the following formula 1 from racemic compound 1 of the following formula 1. [formula 1] The compounds 1a and 1b of the above formula 1 respectively are important intermediates for a process for preparing the respective compounds 2a and 2b of the following formula 2, which are 2,2'-binaphthol-3-aldehyde derivatives. The following compounds 2a and 2b are useful for preparing enantiomerically pure amino acids. The present invention provides a method for preparing the above compounds 1a and 1b very conveniently and economically, and suitably for mass production. [formula 2]

9 Claims, No Drawings

(56) References Cited

OTHER PUBLICATIONS

Notification of Reason for Refusal dated Aug. 24, 2012, regarding Korean Application No. KR10-2010-0118975.
Written Opinion According to Notification of Reasons for Refusal, dated Oct. 10, 2012, regarding Korean Application No. KR10-2010-0118975.
Decision of Grant of Patent dated Feb. 28, 2013, regarding Korean Application No. KR10-2010-0118975.

* cited by examiner

SYNTHETIC METHOD OF ENANTIOMERICALLY PURE 2,2'-DIHYDROXY-1,1'-BINAPHTHYL-3-CARBOXYLIC ACID

CROSS-REFERENCE TO RELATED APPLICATION

This application is a United States National Stage Application under 35 U.S.C. §371 of International Patent Application No. PCT/KR2011/009034, filed Nov. 24, 2011, which claims benefit to Korean Application No. KR 10-2010-0118975, filed Nov. 26, 2010, the entirety of both applications are incorporated herein by reference.

TECHNICAL FIELD

The present invention relates to an optical resolution method and a purification method for preparing enantiomerically pure compounds from 2,2'-dihydroxy-1,1'-binaphthyl-3-carboxylic acid, which is an important intermediate for preparing 2,2'-binaphthol-3-aldehyde derivatives, which method is very convenient and economical, and suitable for mass production.

BACKGROUND ART

Compounds of the following formula 2, which are 2,2'-binaphthol-3-aldehyde, can be very usefully used to separate chiral amino alcohols or amino acids into their respective optical isomers by recognizing their chirality through an imine bond or to convert L-amino acid into D-amino acid or D-amino acid into L-amino acid (see Korean Patent No. 10-0661280; H. Park, K. M. Kim, A. Lee, S. Ham, W. Nam, J. Chin, *J. Am. Chem. Soc.* 2007, 129, 1518-1519; K. M. Kim, H. Park, H. Kim, J. Chin, W. Nam, *Org. Lett.* 2005, 7, 3525-3527).

[formula 2]

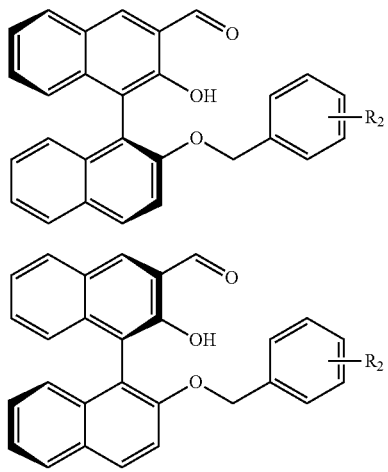

The respective compounds of the formula 2 can be prepared from the enantiomerically pure compounds of the following formula 1 by sequential alkylation of the 2 hydroxyl group, reduction, and oxidation thereof. Since the compounds of the formula 1 can be selectively alkylated at the 2 hydroxyl group, they are useful intermediates that can be alkylated in a high yield without using a protecting group. Thus, it is significantly important to prepare enantiomerically pure compounds 1a and 1b from racemic compound 1 of the formula 1 in an economical way.

[formula 1]

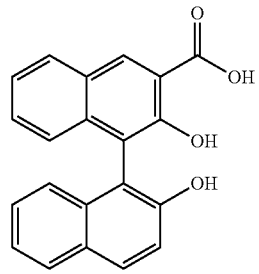

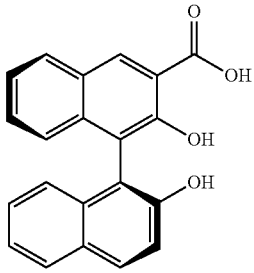

A method of reacting racemic compound 1 of the formula 1 (2,2'-dihydroxy-1,1'-binaphthyl-3-carboxylic acid) with cinchonidine or cinchonine, and filtering and separating the obtained salts using the difference in the solubility of the salts has already been disclosed by Hovorka, M., et al. (Hovorka, M.; Stibor, I; Holakovsky, R.; Smiskova, I.; Struzka, V. Czech Rep. (2001), CZ 287879 B6). However, said method is uneconomical because cinchonidine and cinchonine used in the optical resolution are very expensive. Further, said method requires a large amount of solvents because of bad solubility of the obtained salts, which results in increase in reaction volume and a decrease in productivity. Due to these disadvantages, said method is not suitable for mass production.

DISCLOSURE OF INVENTION

Technical Problem

It is an object of the present invention to solve the above problems of prior art. Thus, it is an object of the present invention to provide a method for preparing enantiomerically pure compounds 1a and 1b using inexpensive chiral amine compounds instead of expensive cinchonidine or cinchonine, which is very convenient and economical, and suitable for mass production.

Solution to Problem

The present invention provides an optical resolution method for economically preparing compounds 1a and 1b of the formula 1 using the difference in the solubility of diastereomeric salts obtained by sequentially using compounds 3a ((S)(−)-1-phenethylamine) and 3b ((R)(+)-1-phenethylamine) of the formula 3, which are inexpensive chiral amines.

[formula 3]

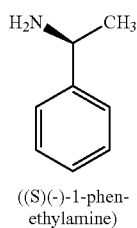

3a ((S)(-)-1-phenethylamine)

Further, the present invention provides a purification method of recrystallizing optically resolved compounds 1a and 1b to remove racemic compounds to prepare enantiomerically pure compounds.

Advantageous Effects of Invention

The present invention provides a method for preparing enantiomerically pure compounds 1a and 1b from the compound 1 of the formula 1, which is very convenient and economical, and suitable for mass production. Therefore, if the method is applied to production lines of an industrial scale, significant effects can be achieved.

MODE FOR THE INVENTION

The present invention provides an optical resolution method of racemic compound 1 of the formula 1.

[Reaction formula 1]

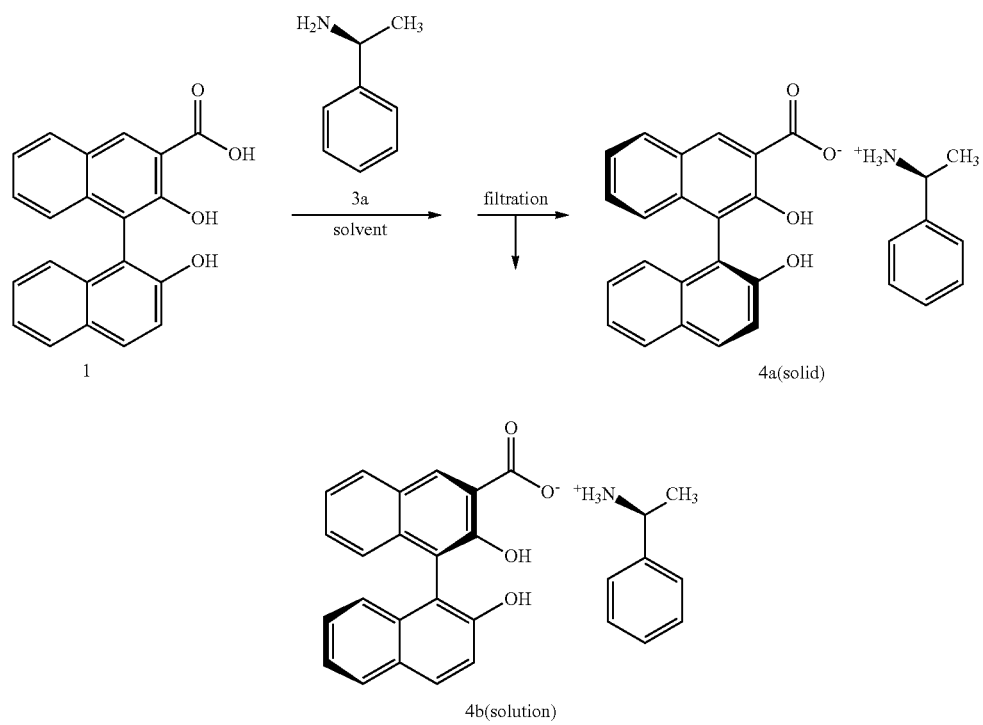

-continued

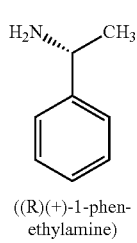

3b ((R)(+)-1-phenethylamine)

As shown in the above reaction formula 1, diastereomeric salts are prepared by dissolving compound 1 in an appropriate solvent and reacting it with compound 3a. During this process, compound 4a, whose solubility is relatively low, is precipitated in the form of solid, and the precipitate is filtered and separated to prepare salt 4a (>95% ee) of the optically resolved compound 1a. Methyl isobutyl ketone, acetonitrile, toluene, etc. are suitable as the solvents used in the reaction of compound 1 with compound 3a, which may be used alone or as a mixture thereof. A mixture solvent of methyl isobutyl ketone and acetonitrile would be preferable.

[Reaction formula 2]

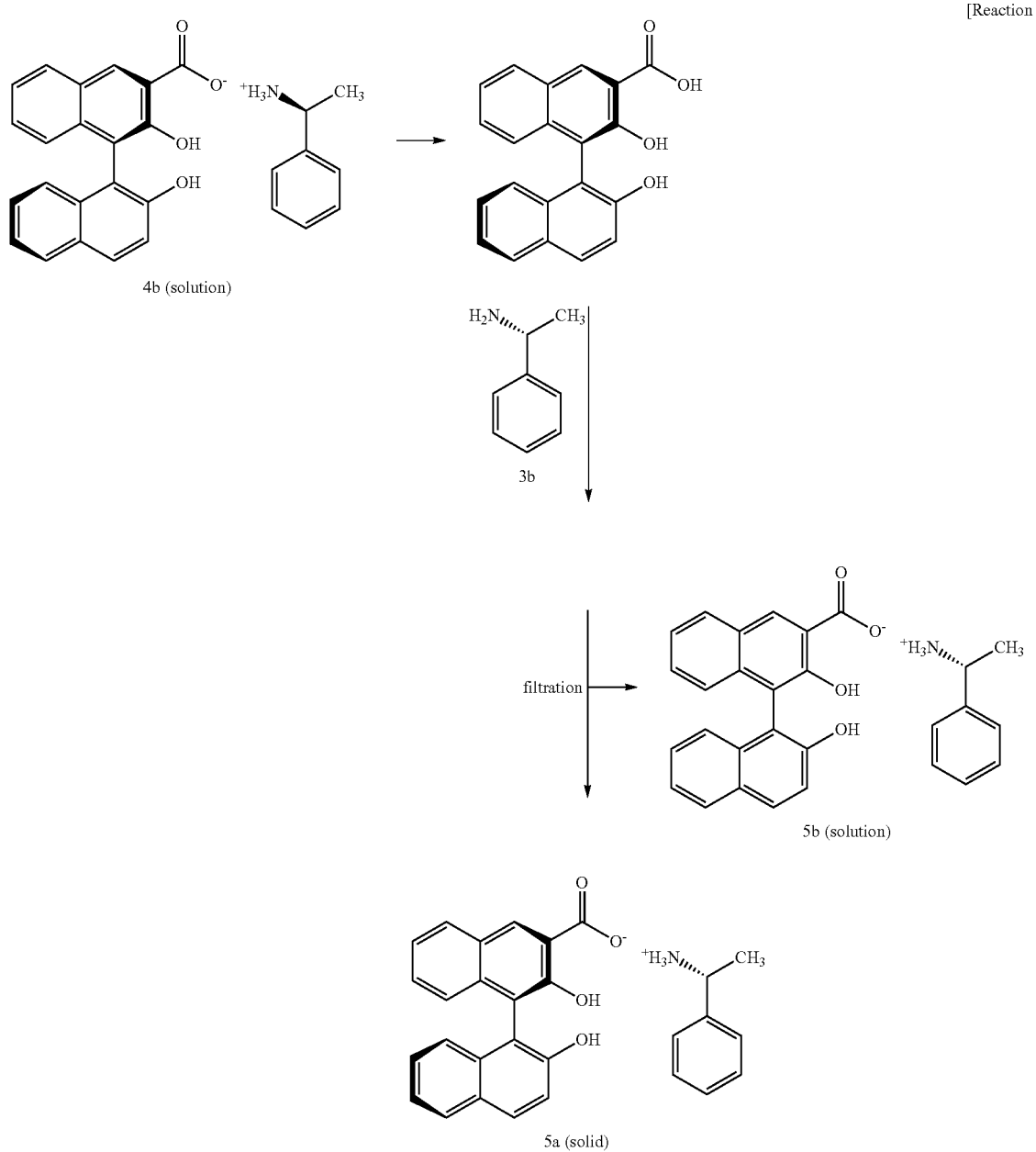

Further, salt 5a of the optically resolved compound 1b can be prepared from the compound 4b (>60% ee) solution of the above reaction formula 1. As shown in the above reaction formula 2, compound 5a, whose solubility is relatively low, is precipitated in the form of solid by washing the compound 4b solution with aqueous hydrochloric acid and reacting it with compound 3b, and then, the precipitate is filtered and separated to prepare salt 5a (>95% ee) of the optically resolved compound 1b.

In addition, if chiral amine 3b is used in reaction formula 1, instead of chiral amine 3a, salt 5a (>95% ee) of the optically resolved compound 1b which is separated in the form of solid can be prepared. Then, if the filtrate is reacted with chiral amine 3a using the method of reaction formula 2, salt 4a (>95% ee) of the optically resolved compound 1a which is separated in the form of solid can be prepared.

Thus, the present invention may use chiral amine 3a or 3b alone or may use chiral amines 3a and 3b successively in optical resolution, and in the case of using them successively, the reaction order is not limited.

In addition, the present invention provides a method for preparing enantiomerically pure compound 1a or 1b, respectively by neutralizing compound 4a or 5a with aqueous hydrochloric acid and increasing optical purity.

[Reaction formula 3]

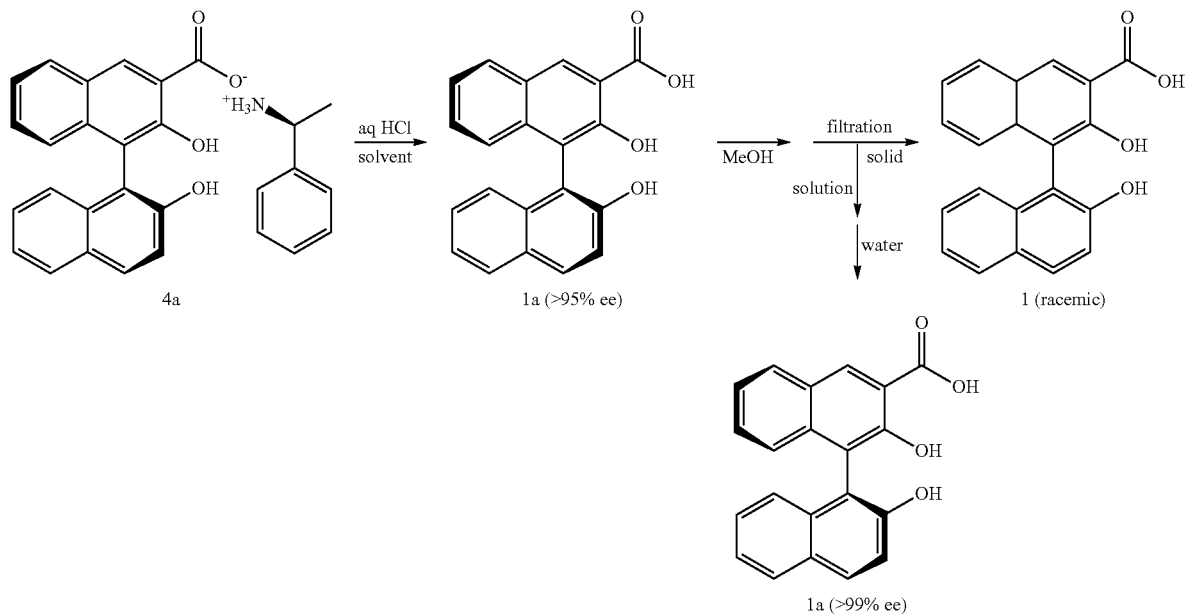

As shown in the above reaction formula 3, the compound 4a (>95% ee) (or 5a) is dissolved in a suitable solvent and washed with aqueous hydrochloric acid to remove phenethylamine 3a (or 3b) that was used in optical resolution. After removing the solvent by concentrating the organic layers, they are dissolved in methanol, and the precipitated racemic compound is filtered and removed, and then, the solid that is precipitated by adding water is filtered to prepare enantiomerically pure compound 1a (>99% ee) (or 1b). Any solvent can be used as an organic solvent for the step of washing with aqueous hydrochloric acid as long as the solvent is not miscible with water and can dissolve compound 1a (or 1b). Methyl isobutyl ketone (MIBK), methyl t-butyl ether (MTBE), methylene chloride, ethyl acetate, etc. would be preferable.

Below, the present invention is explained in detail using examples. However, the following examples are only for exemplifying the present invention, and the present invention is not limited by the following examples.

EXAMPLES

Example 1

Preparation of Salt of (S)-2,2'-Dihydroxy-1,1'-Binaphthyl-3-Carboxylic Acid(S)(+1-Phenethylamine (Compound 4a)

After dissolving racemic 2,2'-dihydroxy-1,1'-binaphthyl-3-carboxylic acid (compound 1) (30.0 g, 90.8 mmol) which is prepared by applying and improving a known method [M. Noji, M. Nakajima and K. Koga. Tetrahedron Lett. 35 (1994), p. 7983-7984] in 330 mL of MIBK/acetonitrile (10/1, v/v), (S)(−)-1-phenethylamine (compound 3a) (5.50 g, 45.4 mmol) was added, and the mixture was stirred for two hours. After further adding compound 3a (2.75 g, 22.7 mmol) thereto, the mixture was stirred for two hours. Then, after further adding compound 3a (2.75 g, 22.7 mmol) thereto, the mixture was stirred for three hours. Thereafter, the precipitated solid was filtered to obtain 16.5 g of the subject compound 4a (36.5 mmol, 96.6% ee) at a yield of 80.4%.

$^1$H NMR (DMSO-$d_6$, 400 MHz) δ8.47 (s, 1H, ArH), 7.93~7.83 (m, 1H, ArH), 7.82 (d, 2H, ArH), 7.51 (d, 2H, ArH), 7.42 (t, 2H, ArH), 7.40~7.30 (m, 2H, ArH), 7.23~7.12 (m, 4H, ArH), 6.97 (d, 1H, ArH), 6.87 (d, 1H, ArH), 4.44 (q, 1H, CH), 1.53 (d, 3H, CH$_3$).

HPLC analysis condition (optical purity); analysis instrument: HPLC (Agilent 1200 series); column: Chiralcel OJ-RH (4.6×150 mm, Daicel), temperature (40° C.); solvent: 40% acetonitrile/H$_2$O (0.1% H$_3$PO4) (4/6, v/v), flow rate: 1.0 mL/min, detection wave length: 210 nm (or 230 nm).

The filtrate was used for the preparation of salt of (R)-2,2-dihydroxy-1,1'-binaphthyl-3-carboxylic acid·(R)(+)-1-phenethylamine (compound 5a) in the following Example 2.

Example 2

Preparation of a Salt of (R)-2,2'-Dihydroxy-1,1'-Binaphthyl-3-Carboxylic Acid·(R)(+)-1-Phenethylamine (Compound 5a)

After adding 6% of HCl solution (60 mL) to the filtrate of the above Example 1 and stirring the mixture for 30 minutes, organic layers were separated and washed with 3% of HCl (60 mL) and water (60 mL) sequentially. The organic layers were dried by anhydrous magnesium sulfate and filtered. Acetonitrile (30 mL) was added, (R)(+)-1-phenethylamine (compound 3b) (4.40 g, 36.3 mmol) was added, and the mixture was stirred for two hours. After further adding compound 3b (2.20 g, 18.2 mmol), the mixture was stirred for three hours. Thereafter, the precipitated solid was filtered to obtain 15.5 g of salt of (R)-2,2'-dihydroxy-1,1'-binaphthyl-3-carboxylic acid ·(R)(+)-1-phenethylamine (compound 5a) (34.3 mmol, 95.5% ee) at a yield of 75.6%.

$^1$H NMR (DMSO-$d_6$, 400 MHz) δ8.47 (s, 1H, ArH), 7.93~7.83 (m, 1H, ArH), 7.82 (d, 2H, ArH), 7.51 (d, 2H,

ArH), 7.42 (t, 2H, ArH), 7.40~7.30 (m, 2H, ArH), 7.23~7.12 (m, 4H, ArH), 6.97 (d, 1H, ArH), 6.87 (d, 1H, ArH), 4.44 (q, 1H, CH), 1.53 (d, 3H, CH$_3$).

Example 3

Preparation of (S)-2,2'-Dihydroxy-1,1'-Binaphthyl-3-Carboxylic Acid (Compound 1a)

Compound 4a (15.0 g, 33.2 mmol, 96.6% ee) was added to methyl t-butyl ether (MTBE) (120 mL), and while stiring the mixture, 6% of aqueous hydrochloric acid (60 mL) was added thereto. After stirring the mixture for one hour at room temperature and separating layers, the organic layers were washed with water (60 mL). The organic layers were concentrated under reduced pressure, methanol (60 mL) was added thereto, and the mixture was stirred for one hour. The precipitated solid was filtered and removed. The filtrate was slowly added to water (120 mL). The precipitated solid was filtered and dried at 80° C. to obtain the subject compound 1a (10.2 g, 30.9 mmol, 99.1% ee) at a yield of 93%.
$^1$H NMR (DMSO-d$_6$, 400 MHz) δ11.09 (s, 1H, OH), 9.17 (s, 1H, OH), 8.72 (s, 1H, ArH), 8.08-8.03 (m, 1H, ArH), 7.86 (t, 2H, ArH), 7.37~7.28 (m, 3H, ArH), 7.26~7.15 (m, 2H, ArH), 6.99~6.91 (m, 2H, ArH).

Example 4

Preparation of (R)-2,2'-Dihydroxy-1,1'-Binaphthyl-3-Carboxylic Acid (Compound 1b)

The subject compound 1b (10.3 g, 31.2 mmol, 99.0% ee) was obtained at a yield of 91% using compound 5a (15.5 g, 34.3 mmol, 95.5% ee) by the same method as in the Example 3 above.
$^1$H NMR (DMSO-d$_6$, 400 MHz) δ11.10 (s, 1H, OH), 9.27 (s, 1H, OH), 8.70 (s, 1H, ArH), 8.08~8.04 (m, 1H, ArH), 7.86 (t, 2H, ArH), 7.35~7.30 (m, 3H, ArH), 7.26~7.15 (m, 2H, ArH), 6.98~6.91 (m, 2H, ArH).

The invention claimed is:

1. A method for preparing a diastereomic salt of 1-phenyl amine 2,2'-dihydroxy-1,1'-binaphthyl-3-carboxylate comprising:
    forming a solution by dissolving racemic 2,2'-dihydroxy-1,1'-binaphthyl-3-carboxylic acid in an organic solvent;
    adding a chiral 1-phenethylamine into the solution and reacting the chiral 1-phenethylamine with the racemic 2,2'-dihydroxy-1,1'-binaphthyl-3-carboxylic acid to form a solid precipitant comprising a diastereomic salt of 1-phenyl amine 2,2'-dihydroxy-1,1'-binaphthyl-3-carboxylate and a supernatant; and
    separating the thus formed solid precipitant from the supernatant to recover the diastereomic salt of 1-phenyl amine 2,2'-dihydroxy-1,1'-binaphthyl-3-carboxylate.

2. The method according to claim 1, wherein the chiral 1-phenethylamine is (S)(−)-1-phenyl amine and the diastereomic salt of the 1-phenyl amine 2,2'-dihydroxy-1,1'-binaphthyl-3-carboxylate is (S)(−)-1-phenyl amine (S) 2,2'-dihydroxy-1,1'-binaphthyl-3-carboxylate.

3. The method according to claim 1, wherein the chiral 1-phenethylamine is (R)(+)-1-phenethylamine and the diastereomic salt of the 1-phenyl amine 2,2'-dihydroxy-1,1'-binaphthyl-3-carboxylate is (R)(+)-1-phenyl amine (R) 2,2'-dihydroxy-1,1'-binaphthyl-3-carboxylate.

4. A method for preparing a diastereomic salt of 1-phenyl amine 2,2'-dihydroxy-1,1'-binaphthyl-3-carboxylate comprising:
    forming a solution by dissolving racemic 2,2'-dihydroxy-1,1'-binaphthyl-3-carboxylic acid in an organic solvent;
    adding a chiral 1-phenethylamine into the solution and reacting the chiral 1-phenethylamine with the racemic 2,2'-dihydroxy-1,1'-binaphthyl-3-carboxylic acid to form a solid precipitant comprising a diastereomic salt of 1-phenyl amine 2,2'-dihydroxy-1,1'-binaphthyl-3-carboxylate and a supernatant;
    separating the thus formed solid precipitant from the supernatant to recover the diastereomic salt of 1-phenyl amine 2,2'-dihydroxy-1,1'-binaphthyl-3-carboxylate; and
    neutralizing a solution comprising the diastereomic salt 1-phenyl amine 2,2'-dihydroxy-1,1'-binaphthyl-3-carboxylate to form an enantiomeric ally pure 2,2'-dihydroxy-1,1'-binaphthyl-3-carboxylic acid.

5. The method according to claim 4, wherein the diastereomic salt of 1-phenyl amine 2,2'-dihydroxy-1,1'-binaphthyl-3-carboxylate is neutralized using hydrochloric acid.

6. A method for preparing a diastereomic salt of 1-phenyl amine 2,2'-dihydroxy-1,1'-binaphthyl-3-carboxylate comprising:
    forming a solution by dissolving racemic 2,2'-dihydroxy-1,1'-binaphthyl-3-carboxylic acid in an organic solvent;
    adding (S)(−)-1-phenyl amine into the solution and reacting the (S)(−)-1-phenyl amine with the racemic 2,2'-dihydroxy-1,1'-binaphthyl-3-carboxylic acid to form a solid precipitant comprising a diastereomic salt of (S)(−)-1-phenyl amine (S) 2,2'-dihydroxy-1,1'-binaphthyl-3-carboxylateand a supernatant;
    separating the thus formed solid precipitant from the supernatant to recover the diastereomic salt of (S)(−)-1-phenyl amine (S) 2,2'-dihydroxy-1,1'-binaphthyl-3-carboxylate; and
    neutralizing a solution of the (S)(−)-1-phenyl amine (S) 2,2'-dihydroxy-1,1'-binaphthyl-3-carboxylate to form enantiomerically pure (S) 2,2'-dihydroxy-1,1'-binaphthyl-3-carboxylic acid.

7. The method according to claim 6, wherein the (S)(−)-1-phenyl amine (S) 2,2'-dihydroxy-1,1'-binaphthyl-3-carboxylate is neutralized using hydrochloric acid.

8. The method according to claim 7, further comprising neutralizing a solution of the (R)(+)-1-phenyl amine (S) 2,2'-dihydroxy-1,1'-binaphthyl-3-carboxylate to form enantiomerically pure (R) 2,2'-dihydroxy-1,1'-binaphthyl-3-carboxylic acid.

9. The method according to claim 8, wherein the (R)(+)-1-phenyl amine (R) 2,2'-dihydroxy-1,1'-binaphthyl-3-carboxylate is neutralized using hydrochloric acid.

* * * * *